United States Patent
Eckert et al.

(10) Patent No.: US 12,251,182 B2
(45) Date of Patent: *Mar. 18, 2025

(54) SURGICAL TOOL POSITIONING BASED ON SENSED PARAMETERS

(71) Applicant: Cilag GmbH International, Zug (CH)

(72) Inventors: Chad E. Eckert, Milford, OH (US); Jason L. Harris, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/382,853

(22) Filed: Oct. 23, 2023

(65) Prior Publication Data

US 2024/0130807 A1 Apr. 25, 2024
US 2024/0225757 A9 Jul. 11, 2024

Related U.S. Application Data

(63) Continuation of application No. 16/552,413, filed on Aug. 27, 2019, now Pat. No. 11,793,582, which is a
(Continued)

(51) Int. Cl.
*A61B 18/08* (2006.01)
*A61B 18/00* (2006.01)
(Continued)

(52) U.S. Cl.
CPC ............ *A61B 34/30* (2016.02); *A61B 18/082* (2013.01); *A61B 18/085* (2013.01);
(Continued)

(58) Field of Classification Search
CPC ..... A61B 18/082; A61B 18/085; A61B 34/30; A61B 201/800791
See application file for complete search history.

(56) References Cited

U.S. PATENT DOCUMENTS 6,493,608 B1 12/2002 Niemeyer
7,344,498 B1 3/2008 Doughty et al.
(Continued)

FOREIGN PATENT DOCUMENTS

CN 1672630 A 9/2005
CN 101045015 A 10/2007
(Continued)

OTHER PUBLICATIONS

Correlated Solutions, "Principle of Digital Image Correlation", Available at: http://correlatedsolutions.com/digital-image-correlation, 2013, 5 pages.
(Continued)

*Primary Examiner* — Daniel W Fowler
*Assistant Examiner* — Annie L Shoulders
(74) *Attorney, Agent, or Firm* — Mintz, Levin, Cohn, Ferris, Glovsky and Popeo, P.C.

(57) ABSTRACT

Devices, systems, and methods are provided in which movement of a tool is controlled based on sensed parameters. In one embodiment, an electromechanical tool is provided having an instrument shaft and an end effector formed thereon. The electromechanical tool is configured to be mounted on an electromechanical arm, and the electromechanical tool is configured to move with or relative to the electromechanical arm and perform surgical functions. A controller is operatively coupled to the electromechanical arm and the electromechanical tool and is configured to retard advancement of the electromechanical tool toward a tissue surface based on a sensed amount of displacement of a tissue surface, a strain on the tissue of the patient, the temperature of the electromechanical tool, or the like.

14 Claims, 5 Drawing Sheets

Related U.S. Application Data continuation of application No. 15/238,001, filed on Aug. 16, 2016, now Pat. No. 10,398,517.

(51) Int. Cl.
  *A61B 34/30* (2016.01)
  *A61B 17/00* (2006.01)
  *A61B 90/00* (2016.01)
  *B25J 9/16* (2006.01)

(52) U.S. Cl.
  CPC ............... *A61B 2017/00084* (2013.01); *A61B 2018/00791* (2013.01); *A61B 2090/0427* (2016.02); *B25J 9/1676* (2013.01); *G05B 2219/40415* (2013.01)

(56) References Cited

U.S. PATENT DOCUMENTS

| | | |
|---|---|---|
| 8,114,345 B2 | 2/2012 | Dlugos, Jr. et al. |
| 8,206,380 B2 | 6/2012 | Lenihan et al. |
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 8,999,371 B2 | 4/2015 | Lu et al. |
| 9,311,566 B2 | 4/2016 | Iliopoulos et al. |
| 10,398,517 B2 | 9/2019 | Eckert et al. |
| 10,537,399 B2 | 1/2020 | Eckert et al. |
| 11,793,582 B2 * | 10/2023 | Eckert .................... G16H 40/63 |
| 2005/0234336 A1 | 10/2005 | Beckman et al. |
| 2008/0081948 A1 | 4/2008 | Weisenburgh et al. |
| 2009/0024023 A1 | 1/2009 | Welches et al. |
| 2009/0248037 A1 | 10/2009 | Prisco |
| 2010/0169815 A1 | 7/2010 | Zhao et al. |
| 2011/0046476 A1 | 2/2011 | Cinquin et al. |
| 2011/0118709 A1 | 5/2011 | Burbank |
| 2011/0118778 A1 | 5/2011 | Burbank |
| 2011/0295247 A1 | 12/2011 | Schlesinger et al. |
| 2011/0319751 A1 | 12/2011 | Groszmann |
| 2012/0071863 A1 | 3/2012 | Lee et al. |
| 2012/0143380 A1 | 6/2012 | Weinhardt et al. |
| 2013/0116681 A1 | 5/2013 | Zhang |
| 2013/0123801 A1 | 5/2013 | Umasuthan et al. |
| 2013/0199540 A1 | 8/2013 | Buske |
| 2013/0282052 A1 | 10/2013 | Aranyi et al. |
| 2013/0338664 A1 | 12/2013 | Wang et al. |
| 2014/0005684 A1 | 1/2014 | Kim et al. |
| 2014/0005718 A1 | 1/2014 | Shelton, IV et al. |
| 2014/0222207 A1 | 8/2014 | Bowling et al. |
| 2015/0374446 A1 | 12/2015 | Malackowski et al. |
| 2016/0136390 A1 | 5/2016 | Flanagan et al. |
| 2016/0278765 A1 | 9/2016 | Shelton, IV et al. |
| 2017/0000541 A1 | 1/2017 | Yates et al. |
| 2017/0296173 A1 | 10/2017 | Shelton, IV et al. |

FOREIGN PATENT DOCUMENTS

| | | |
|---|---|---|
| CN | 101589290 A | 11/2009 |
| CN | 104379681 A | 2/2015 |
| CN | 104582629 A | 4/2015 |
| CN | 104736090 A | 6/2015 |
| CN | 104736092 A | 6/2015 |
| EP | 1579878 A1 | 9/2005 |
| EP | 1839599 A1 | 10/2007 |
| WO | 2007033206 A2 | 3/2007 |
| WO | 2016064632 A1 | 4/2016 |
| WO | 2018034972 A1 | 2/2018 |

OTHER PUBLICATIONS

ISRWO, "International Search Report and Written Opinion received for PCT Application No. PCT/US2017/046461", mailed on Oct. 26, 2017, 10 pages.

ISRWO, "International Search Report and Written Opinion received for PCT Application No. PCT/US2017/046468", mailed on Nov. 27, 2017, 14 pages.

Kennedy et al., "A Vision-Based Approach for Estimating Contact Forces: Applications to Robot-Assisted Surgery", Applied Bionics and Biomechanics, 2005, vol. 2, No. 1, pp. 53-60.

* cited by examiner

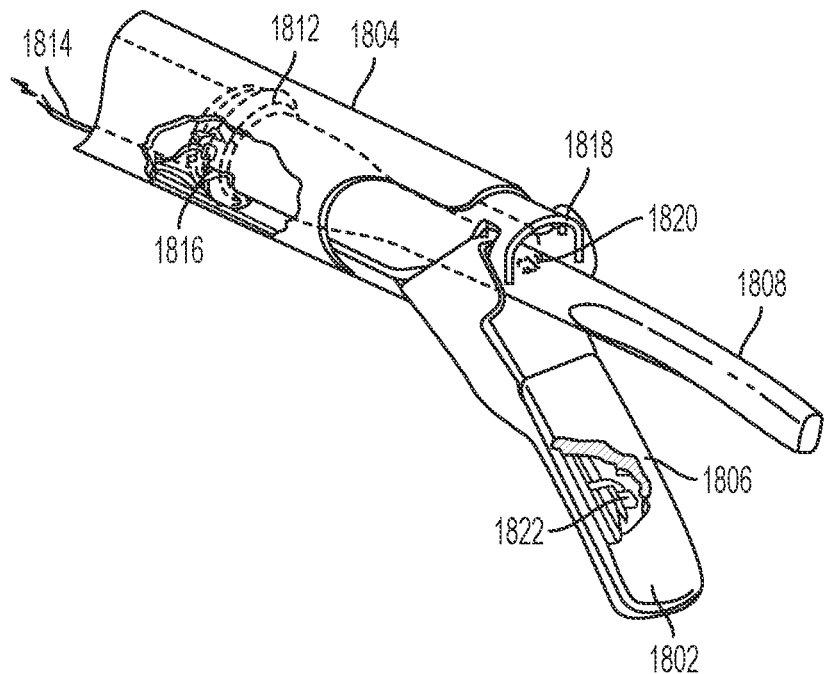

FIG. 5

APPLYING AT LEAST ONE TYPE OF ENERGY TO A TISSUE USING AN END EFFECTOR FORMED ON AN INSTRUMENT SHAFT OF AN ELECTROMECHANICAL TOOL, THE ELECTROMECHANICAL TOOL BEING CONFIGURED TO BE MOUNTED ON AN ELECTROMECHANICAL ARM

RECEIVING, DURING AN APPLICATION OF THE AT LEAST ONE TYPE OF ENERGY TO THE TISSUE, A SENSED TEMPERATURE OF THE END EFFECTOR

REDUCING, BASED ON THE SENSED TEMPERATURE, A VELOCITY OF THE ELECTROMECHANICAL TOOL TOWARD A TISSUE SURFACE

FIG. 6

SURGICAL TOOL POSITIONING BASED ON SENSED PARAMETERS

CROSS REFERENCE TO RELATED APPLICATION

This application is a continuation of U.S. patent application Ser. No. 16/552,413, filed on Aug. 27, 2019 and entitled "SURGICAL TOOL POSITIONING BASED ON SENSED PARAMETERS," which is a continuation of U.S. patent application Ser. No. 15/238,001, filed Aug. 16, 2016, entitled "Surgical Tool Positioning Based on Sensed Parameters," which are hereby incorporated herein by reference in their entireties.

FIELD OF THE INVENTION

Methods and devices are provided for robotic surgery, and in particular for positioning surgical tools based on sensed parameters.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is provided with an image of the surgical site on a visual display at a location remote from the patient. The surgeon can typically perform the surgical procedure at the location remote from the patient whilst viewing the end effector movement on the visual display during the surgical procedure. While viewing an image of the surgical site on the visual display, the surgeon performs the surgical procedures on the patient by manipulating master control devices at the remote location to control motion of the remotely controlled instruments.

While significant advances have been made in the field of robotic surgery, there remains a need for improved methods, systems, and devices for use in robotic surgery.

SUMMARY OF THE INVENTION

Surgical devices, systems, and methods are provided for positioning surgical tools based on sensed parameters. In one embodiment, a surgical system can include one or more of the following components. The surgical system can include an electromechanical arm configured for movement in multiple axes, and an electromechanical tool having an instrument shaft and an end effector formed thereon. The electromechanical tool can be configured to be mounted on the electromechanical arm, and the electromechanical tool can be configured to move with or relative to the electromechanical arm and to apply energy to tissue engaged by the end effector. The surgical system can also include a controller operatively coupled to the electromechanical arm and the electromechanical tool. The controller can be configured to retard advancement of the electromechanical tool toward a tissue surface based on a sensed temperature of the end effector.

In some variations, one or more of the features described herein may be included in the system. A sensor can be provided and it can be configured to sense the temperature of the end effector. The sensor can include an infrared (IR) sensor, a thermocouple disposed on the end effector, a camera, or the like. In other aspects, the surgical system can include a sensor configured to sense a position of the end effector relative to a tissue surface.

The controller can be configured to retard advancement of the electromechanical tool when the temperature is within a predetermined threshold temperature, predetermined threshold distance from a tissue surface, or the like. The threshold distance can be a function of the temperature of the end effector. The system can also include a sensor configured to sense a distance of the end effector from a tissue surface.

In another aspect, a method for operating a system is provided and includes applying energy to a tissue using an end effector formed on an instrument shaft of an electromechanical tool. The electromechanical tool can be mounted on an electromechanical arm. A sensed temperature of the end effector can be received during an application of the energy to the tissue. A velocity of the electromechanical tool, toward a tissue surface, can be reduced based on the sensed temperature.

In some variations, one or more of the following operations may be included in the method. The sensed temperature can be a sensed temperature of the end effector and a sensed temperature of the tissue surface. The velocity can be reduced to a first threshold velocity when the temperature is within a first predetermined temperature range, a second threshold velocity when the temperature is within a second predetermined temperature range, or the like. The first threshold velocity can be adjusted by a first amount in response to determining that the electromechanical tool is a first threshold distance from the tissue surface. The first threshold velocity can be adjusted by a second amount in response to determining that the electromechanical tool is a second threshold distance from the tissue surface.

The velocity can be reduced based on a sensed position of the end effector relative to the tissue surface. The temperature can be sensed by a sensor on the end effector, a sensor on a camera, or the like.

In another aspect, a surgical system is provided having an electromechanical arm configured for movement in multiple axes. The surgical system can include an electromechanical tool having an instrument shaft and an end effector formed thereon. The electromechanical tool can be configured to be mounted on the electromechanical arm, and the electromechanical tool can be configured to move with or relative to the electromechanical arm and to apply energy to tissue engaged by the electromechanical tool. The surgical system can include a controller operatively coupled to the electromechanical arm and the electromechanical tool. The controller can be configured to retard advancement of the electromechanical tool toward a tissue surface based on a sensed amount of displacement of a tissue surface.

In some variations, one or more of the following features can be included in the surgical system. For example, the surgical system can include an applicator having a material configured to be applied onto a tissue surface, the material being configured to indicate a displacement of the tissue surface. In one embodiment, the material can include a bio-absorbable aerosolized particulate material. In other aspects, the sensed amount of displacement can include a strain of the tissue surface. The controller can be configured to retard advancement of the electromechanical tool when the sensed amount of displacement is within a predetermined displacement range.

The system can include a sensor configured to sense an amount of displacement of a tissue surface. The sensor can include a camera.

In another aspect, a method is provided that includes advancing an end effector formed on an instrument shaft of an electromechanical tool toward a tissue surface. The electromechanical tool can be mounted on an electromechanical arm. A sensed amount of displacement of the tissue surface can be received and, based on the sensed amount of displacement, a velocity of the electromechanical tool toward a tissue surface can be reduced.

In some variations, one or more of the following operations and features can be included in the method. The sensed amount of displacement can be obtained by detecting movement of a patterned material deposited onto the tissue surface. The patterned material can provide at least two contrast points. The method can include determining a tissue strain based on the detected movement of the patterned material.

The velocity of the electromechanical tool can be reduced when the sensed amount of displacement exceeds a threshold amount of displacement. The velocity of the electromechanical tool can be reduced to a first threshold velocity when the amount of displacement is within a first predetermined displacement range, to a second threshold velocity when the amount of displacement is within a second predetermined displacement range, or the like.

BRIEF DESCRIPTION OF THE DRAWINGS

The invention will be more fully understood from the following detailed description taken in conjunction with the accompanying drawings, in which:

FIG. 5 is a perspective, partially transparent view of another embodiment of an end effector;

FIG. 6 is a schematic illustrating one exemplary process flow for one embodiment of using an end effector;

DETAILED DESCRIPTION OF THE INVENTION

Figure 1:
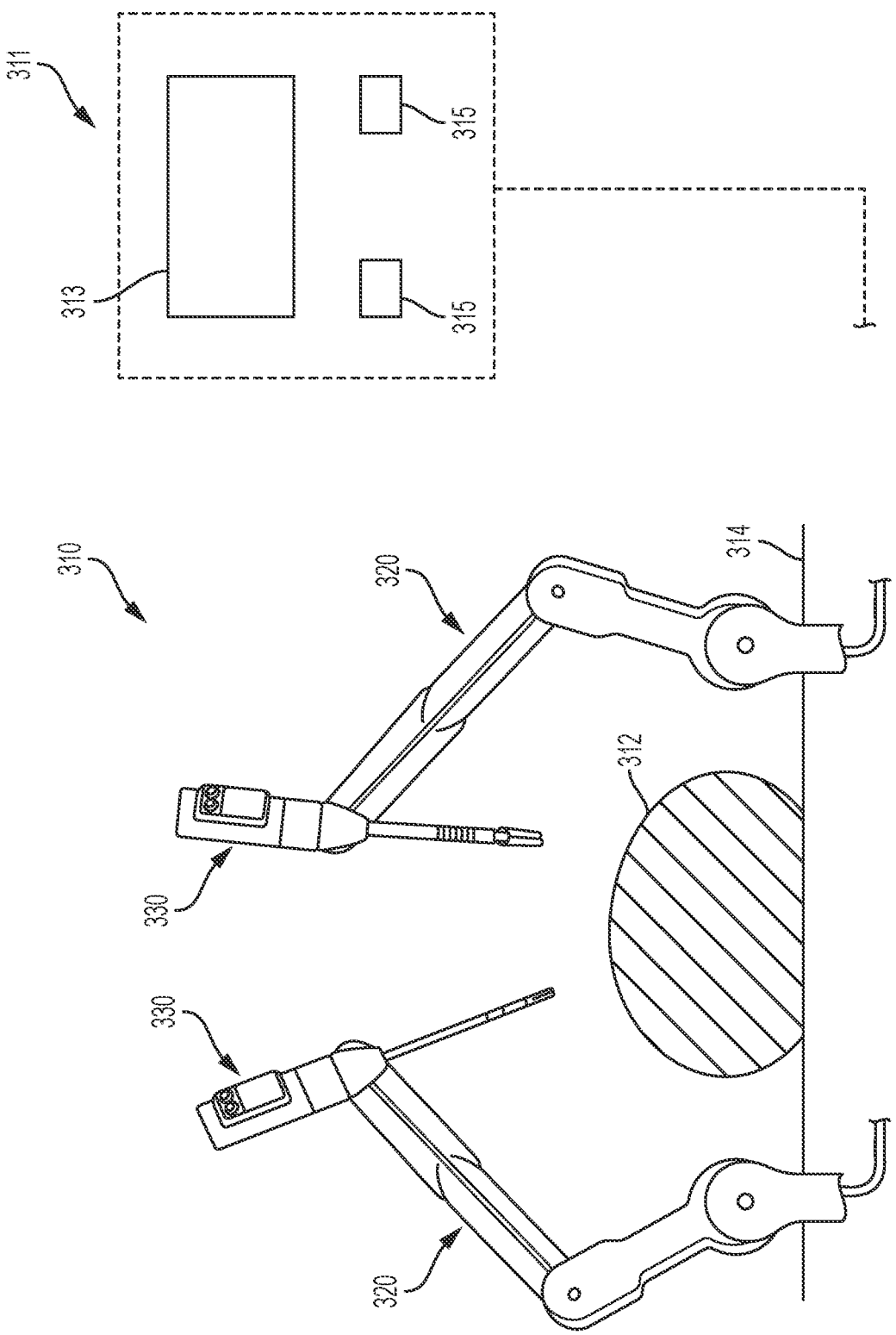
FIG. 1 is a perspective view of one embodiment of a surgical robotic system having a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical systems for positioning surgical tools based on sensed parameters are provided. Robotic surgical tools, such as electromechanical tools, generally have an instrument shaft and an end effector on a distal end thereof. The electromechanical tool is configured to be mounted on an electromechanical arm, and the electromechanical tool is configured to move with or relative to the electromechanical arm and to perform surgical functions. The tool has a plurality of actuators for causing various functions of the end effector, such as rotation, articulation, clamping, energy delivery, etc. The electromechanical arm can electromechanically drive the actuators to control the end effector.

Electromechanical arms and electromechanical tools provided herein have various controllers and mechanisms for retarding advancement of the electromechanical tool toward a tissue surface based on a sensed amount of displacement of a tissue surface, a strain on the tissue of the patient, a temperature of the electromechanical tool, or the like.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

A robotic surgical system consistent with the present description can incorporate a visual sensor and/or camera and an associated viewing field to allow the robotic surgical system to provide any feedback. For example, the robotic surgical system can include an end effector over which the system can have control. The system can provide instructions to the end effector in the form of a declared action (e.g. clamping, energy delivery, etc.). Under ideal surgical conditions, the end effector proceeds with performing the declared action as instructed based on user input instructions. However, under many surgical conditions, the end effector might not be able to perform the declared action as instructed for a variety of reasons and/or it might not be ideal for the end effector to continue to perform the declared actions for a variety of reasons, such as tissue and/or end effector temperature, proximity of the end effector to surrounding tissue, unexpected surgical conditions, human error, etc. The visual sensor and/or camera can be used to detect a variety of parameters of the tool, the end effector, and/or the surrounding tissue. If, for instance, an end effector is heated to an excess degree through use, the heat emanated by the end effector can cause damage to surrounding tissue if the heated end effector contacts or is kept in the vicinity of tissue for too long a period of time. In such a situation, it can be desirable to have a predetermined distance threshold representing the closest distance that the heated end effector can get to surrounding tissue without causing damage. The visual sensor and/or camera can also be used to visually detect at least one visual indicator on the tool, on adjacent tools, and/or on tissue. For example, a visual indicator indicative of a length scale can allow an action of the tool to be visually measured by the camera and transmitted to a corresponding control system, such as the control system 315 described above. The robotic system can modify the action of the tool based on the visually measured action.

Figure 2:
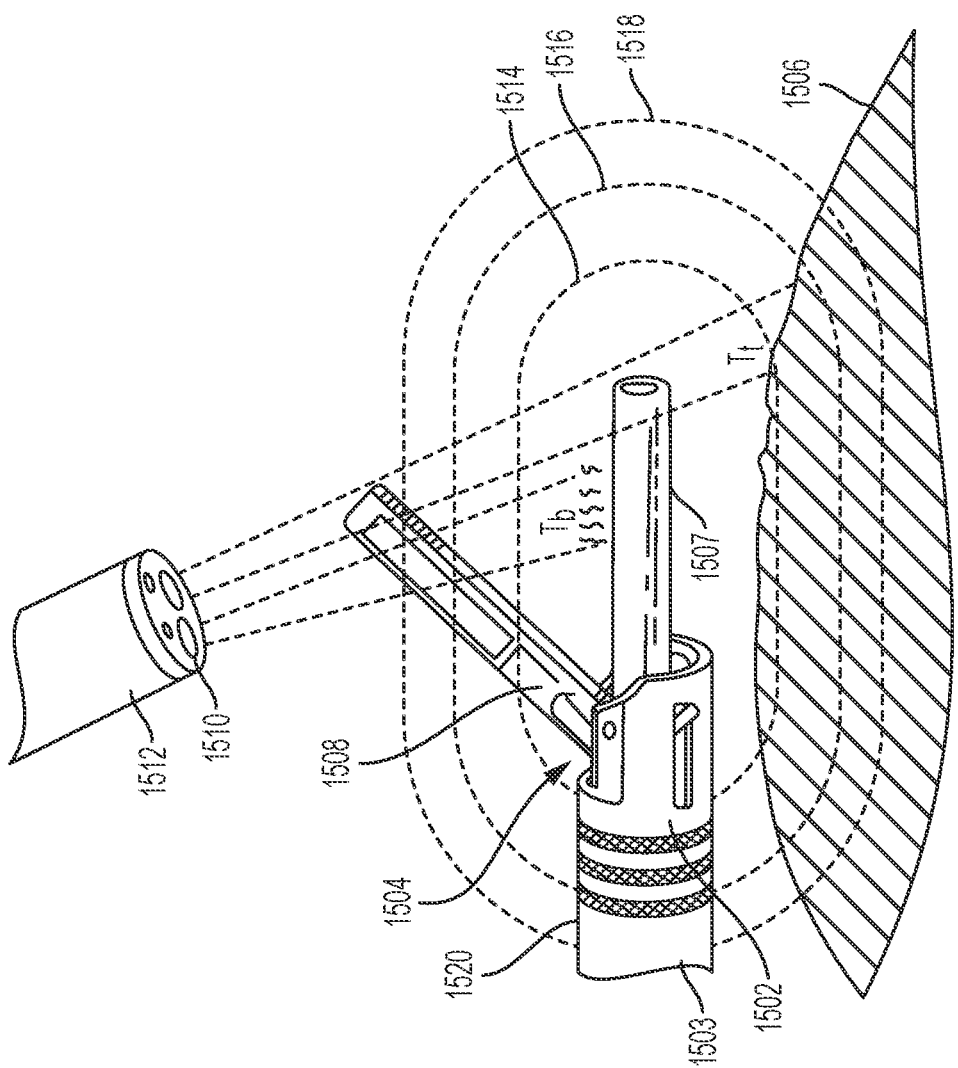
FIG. 2 is a perspective view of one embodiment of a surgical tool with an end effector in the vicinity of patient tissue.

FIG. 2 illustrates one embodiment of an electromechanical tool with a shaft 1503 having a distal end 1502 and an end effector 1504 mounted to the shaft 1503 in the vicinity of patient tissue 1506. The end effector 1504 includes jaws 1507, 1508, with jaw 1507 being in the form of an ultrasonic blade. The shaft 1503 and the end effector 1506 are part of a robotic surgical system, such as the robotic surgical system 300 illustrated in FIG. 1, and can be mounted on an electromechanical arm. The robotic surgical system can include an endoscope, such as binocular scope 1512, having at least one visual sensor 1510. The illustrated visual sensor 1510 is disposed at a distal end of a binocular scope 1512. The illustrated visual sensor 1510 is an infrared sensor, but the visual sensor can be a CCD, a CMOS, or the like. The visual sensor 1510 can be configured to detect the temperature $T_b$ of at least part of the end effector 1504, for example of the ultrasonic blade 1507 of the end effector 1504, and/or the temperature $T_t$ of the tissue 1506 of the patient that is adjacent the end effector 1504. In one aspects, a controller can be configured to compare the temperature $T_b$ of the ultrasonic blade and the temperature $T_t$ of the tissue of the patient and determine distance thresholds 1514, 1516 and 1518 for different temperatures of the end effector 1504. The distance thresholds 1514, 1516 and 1518 can represent a variety of safe and/or non-harmful distances for the tissue 1506 and/or the end effector 1504, such as the closest distance from the tissue 1506 of the patient that the heated end effector 1504 can be positioned without causing damage to the tissue 1506. For example, distance threshold 1514 can represent the closest position an end effector 1504 having a temperature $T_1$ can be positioned with respect to the tissue 1506 of the patient; distance threshold 1516 can represent the closest position an end effector 1504 having a temperature $T_2$ can be positioned with respect to the tissue 1506 of the patient; and distance threshold 1518 can represent the closest position an end effector 1504 having a temperature $T_3$ can be positioned with respect to the tissue 1506 of the patient. Temperature $T_1$ is less than temperature $T_2$ which is less than temperature $T_3$. The temperatures $T_1$, $T_2$, $T_3$ can represent the temperature $T_b$ of the ultrasonic blade 1507 directly or can represent the compared temperatures between the temperature $T_b$ of the ultrasonic blade and the temperature $T_t$ of the tissue. An infrared sensor, such as the Melexis MLX90621, can be integrated into the binocular scope 1512 and/or the end effector 1504, and can act to compare the end effector temperature with an adjacent tissue temperature for an accurate indication of temperature. This process can occur before and/or during and/or after use of the end effector to affect tissue. Force thresholds based on force limits can also be used in addition to or instead of distance thresholds.

The controller, such as controller 315 illustrated in FIG. 1, can be configured to facilitate movement of the end effector 1504 toward the tissue 1506 of the patient. The controller can be configured to determine a position of the end effector 1504 with respect to the tissue 1506 of the patient through the visual sensor 1510. For example, the visual sensor 1510 can obtain an image of the area in the vicinity of the end effector 1504 and/or shaft 1503. The visual sensor 1510 facilitates determination of the position of the end effector 1504 relative to the tissue 1506 of a patient through the use of one or more fixed-size and fixed-space indicators in the form of a visual scale, such as markers 1520 on the shaft 1503. The shaft markers 1520 can have a known thickness and a known separation between markers. Because the lengths and widths are fixed and known, the markers 1520 can be used to determine a length scale and a relative position of the shaft 1503 and/or the end effector 1504 to the tissue 1506 and/or the visual sensor 1512. For example, the images of the markers 1520 can be triangulated and used to determine the location of the shaft 1503 and/or the end effector 1504 to the tissue 1506 and/or the visual sensor 1512.

The controller can therefore be configured to determine the location of the shaft 1503 based on detection by the visual sensor 1510 of the shaft markers 1520. During use, the controller can act to retard advancement of the end effector 1504 and/or the shaft 1503 toward the tissue 1506 based on the sensed temperature of the end effector. For example, the end effector 1504 can be advanced toward the tissue 1506 while temperature is monitored. If the sensed temperature of the end effector 1504 is at or in excess of a predetermined threshold temperature, for example temperature $T_1$, the controller can act to stop the advancement of the end effector 1504 so that the end effector 1504 does not move closer toward the tissue 1506 than a predetermined threshold distance from a tissue 1506, for example the distance threshold 1514. Because the threshold distance 1514 represents the closest that the end effector 1504 having a temperature $T_1$ can get to tissue 1506 without causing damage, the controller can prevent harm to tissue 1506 by slowing or stopping the advancement of the end effector 1504. The threshold distance and/or the threshold temperature can both vary depending on the situation. For example, the sensed temperature of the end effector 1504 may be at or above $T_2$ or $T_3$, and the controller may be configured to stop the advancement of the end effector 1504 so that the end effector 1504 does not move closer to the tissue 1506 than the distance thresholds 1516 or 1518, respectively. While the temperatures in the illustrated embodiment represent comparisons between temperatures of the end effector and/or the ultrasonic blade and the surrounding tissue, the threshold distances may be a function of the temperature of the end effector 1504, the ultrasonic blade, and/or the surrounding tissue without comparison. In some variations, the end effector can move beyond the set distance threshold even when a temperature exceeds a safe threshold, for example a manual override can be provided such that an operator can force the end effector to move past the thresholds if desired.

Although an ultrasonic blade in the end effector 1504 is discussed herein, any end effector and/or any electromechanical tool can be used. The electromechanical tool can have a variety of configurations, such as being configured to apply energy to tissue engaged by the end effector, fire staples, and/or cut tissue.

In some variations, based on the size of the shaft markers 1520 as detected at the visual sensor 1510, a determination can be made as to the location of the shaft 1503 with respect to the location of the visual sensor 1510. In some variations, based on a relative size of patient tissue and/or one or more other objects adjacent the patient tissue and/or the distal end of the shaft 1503, and the size of the shaft markers 1520, a determination can be made as to the location of the end of the shaft 1503 with respect to various surrounding objects, tissues, tools, etc.

Figure 3:
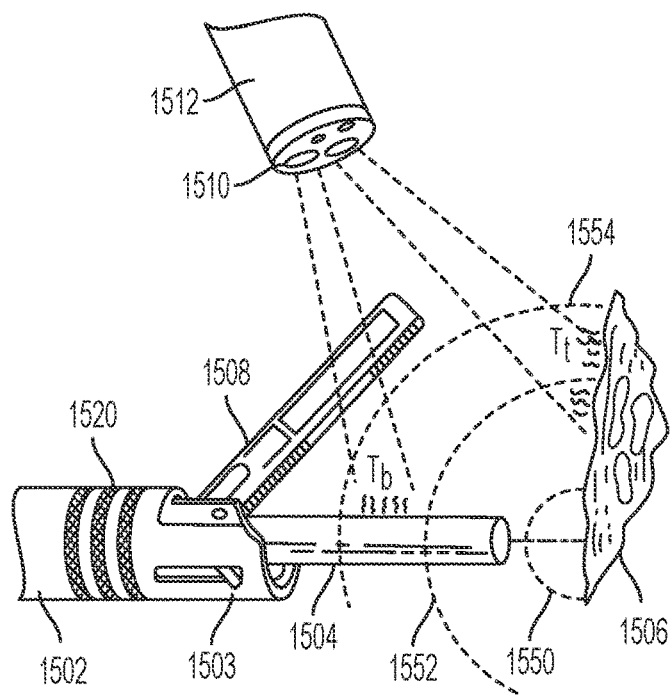
FIG. 3 is a perspective view of the surgical tool of FIG. 2 in the vicinity of tissue.
Figure 4:
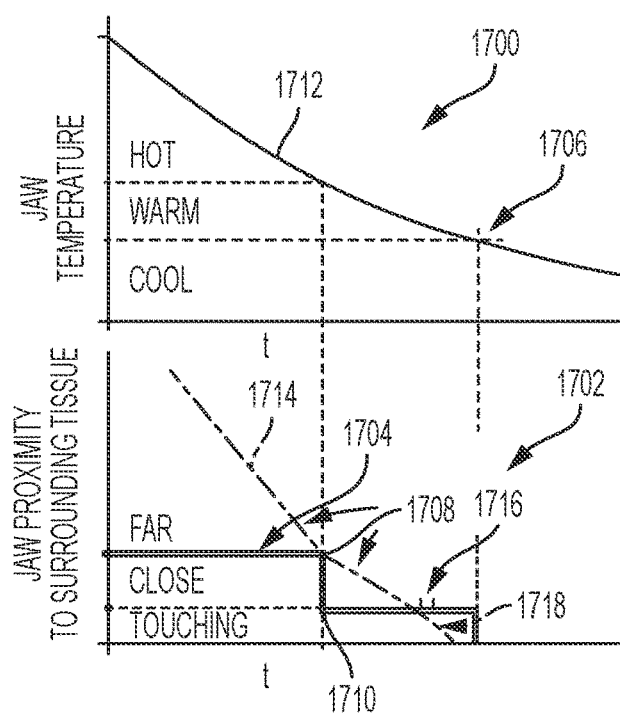
FIG. 4 is a graphical depiction of jaw temperature changes of an end effector over time and jaw proximity changes to patient tissue over time of the end effector of FIG. 2.

While FIG. 2 illustrates measuring threshold distances from the end effector 1504, distances can also be measured from surrounding tissue. For example, FIG. 3 illustrates the end effector 1504 in the vicinity of tissue 1506. However, threshold distances 1550, 1552, and 1554 are measured relative to tissue 1506 instead of the end effector 1504, as is illustrated in FIG. 2. A safe threshold distance of the end effector 1504 from tissue 1506 can thus vary depending on the temperature of the end effector 1504. As illustrated FIG. 4, the controller can be configured to facilitate movement of the end effector 1504 toward the tissue 1506 of the patient at varying distances from the tissue based on temperature. When the temperature of the end effector 1504 is at a highest point (illustrated on the far left of graph 1700 of FIG. 4), the heated end effector 1504 is disposed at a location farthest from tissue 1506 of the patient (illustrated on the far left of graph 1702 of FIG. 4). Thus graph 1702 illustrates the $T_2$ distance threshold 1704. The $T_2$ distance threshold 1704 is the closest distance that the heated end effector 1504 having a temperature $T_2$ can get to the tissue 1506 of the patient without causing damage. As the temperature of the end effector 1504 reduces over time, the end effector 1504 can get closer to tissue 1506 without damaging the tissue 1506. At 1706 the end effector 1504 is at a low enough temperature to be able to touch the tissue 1506 without causing damage to the tissue 1506 (illustrated on the far right of graphs 1700, 1702). With reference to graph 1702, at time 1708 the robotic surgical system can be configured to stop the advance of the end effector 1504 toward the tissue 1506 until the temperature of the end effector 1504 has decreased further. For example, line 1710, illustrated in the graph 1702, represents the closest proximity of the end effector 1504 with respect to the tissue 1506 of the patient when the temperature of the end effector 1504 is below a temperature 1712. When the temperature of the end effector 1504 has a temperature $T_1$, the robotic surgical system can be configured to stop the movement of the end effector 1504 toward the tissue 1506 of the patient at the distance 1514. The distance 1514 is represented by the line 1710 in graph 1702 of FIG. 4. At 1716, the robotic surgical system can be configured to halt the movement of the end effector 1504 toward the tissue 1506. Dashed line 1714 of graph 1702 is an exemplary illustration of the velocity of end effector 1504. As the end effector 1504 approaches tissue 1506, the velocity of end effector 1504 can be configured to be reduced to ensure the controller and the overall robotic system can stop the end effector 1504 at selected distance thresholds. In some variations, an alert can be provided to the operator of the robotic surgical system that the heated end effector 1504 has reached a threshold distance.

As discussed above, the robotic surgical system can be configured to allow manual override by the operator of the robotic surgical system. For example, the robotic surgical system can stop the end effector 1504 at a particular distance threshold if the blade of the end effector 1504 exceeds a desired temperature. The system can cause a signal or notice to the operator, such as vibration of controls, visual and/or tactile and/or auditory feedback, etc., indicating that the system has stopped all movement because a distance threshold has been reached. If the operator wishes to reinstate motion and effectively ignore the threshold, the system can be configured to receive an input from the operator causing the robotic surgical system to move the end effector 1504 closer toward the tissue 1506 of the patient than a threshold distance would normally allow. Line 1718 of graph 1702 is an exemplary illustration of the velocity of the end effector 1504 after manual override by the operator of the robotic surgical system. This situation may be desirable for a variety of reasons, such as cauterizing cut tissue or an emergency surgical situation.

FIG. 5 illustrates another embodiment of a surgical tool with an end effector 1802 coupled to a tool shaft 1804. The end effector 1802 includes first and second jaws 1806, 1808. Jaw 1808 can be in the form of a cutting blade or jaw for delivering energy and cutting tissue grasped between jaws 1806, 1808. A robotic surgical system with a controller, such as robotic surgical system 300 illustrated in FIG. 1, can be configured to control the end effector 1802. The end effector 1802 can couple with the tool shaft 1804 at a coupling 1812. Various actuators can extend through the tool shaft 1804 for clamping the jaws. The controller can control and/or power a variety of functions in the end effector 1802. The end effector 1802 can be similar to the end effector 1504, however, the end effector 1802 can incorporate one or more sensors therein to assist in measuring temperature. For example, a temperature sensor 1816 can be disposed in the tool shaft 1804 at the coupling 1812, temperature sensor 1818 can be disposed in the vicinity of a proximal end of the jaws 1806, 1808, and a temperature sensor 1822 can be disposed within the jaw 1806 of the end effector 1802. The sensors can take a variety of forms, such as thermocouples and/or infrared sensors. For instance, the temperature sensor 1818 can be an infrared sensor and can measure temperature at a portion 1820 of the jaw 1808. The temperature sensors 1816, 1818, and/or 1822 can be electrically connected to the controller. For example, a wire 1814 disposed within the tool shaft 1804 can be configured to couple to one or more sensors in the end effector. The controller can be configured to receive signals generated by the temperature sensors 1816, 1818, and/or 1822 including temperature information indicative of the temperature of the end effector 1802. The temperature information can then be used by the controller to control movement of the end effector 1802 toward tissue, as described above regarding the end effector 1504. Temperature readings from visual sensors, such as infrared cameras, of objects that are reflective and/or shiny, such as a cutting blade, can sometimes be less reliable than may be desired in an operating situation. In such a situation, temperature sensors incorporated into the end effector itself and/or a shaft can assist the system to get accurate measurements. For example, a temperature sensor, such as thermocouple instrumentation, near a blade of an end effector can allow the system to take an accurate temperature reading of the blade and proceed accordingly.

As illustrated in FIG. 6, in use, at least one type of energy can be applied to a tissue using an end effector (such as any of the end effectors described herein) formed on an instrument shaft of an electromechanical tool. During application of the at least one type of energy to the tissue, a temperature of the end effector can be sensed and communicated to a controller. The sensed temperature can be used by the controller to control movement of the tool shaft and/or end effector as described herein. The sensed temperature can comprise a sensed temperature of the end effector and/or a sensed temperature of the tissue surface. In some variations, the temperature can be sensed by a sensor on the end effector itself. In some variations, the temperature can be sensed by a sensor on a camera. Based on the sensed temperature, a velocity of the end effector toward a tissue surface can be reduced. The movement of the electromechanical tool toward the tissue of a patient can be halted at distance thresholds from the tissue. The distance thresholds can be functions of the temperature of the end effector as described above. In some variations, the velocity of an end effector can be reduced to a first threshold velocity when the temperature is within a first predetermined temperature range. The first threshold velocity can be adjusted in response to determining that the electromechanical tool is at a first threshold distance from the tissue surface. The velocity can be reduced to a second threshold velocity when the temperature is within a second predetermined temperature range. The first threshold velocity can be adjusted in response to determining that the electromechanical tool is a second threshold distance from the tissue surface.

Figure 7:
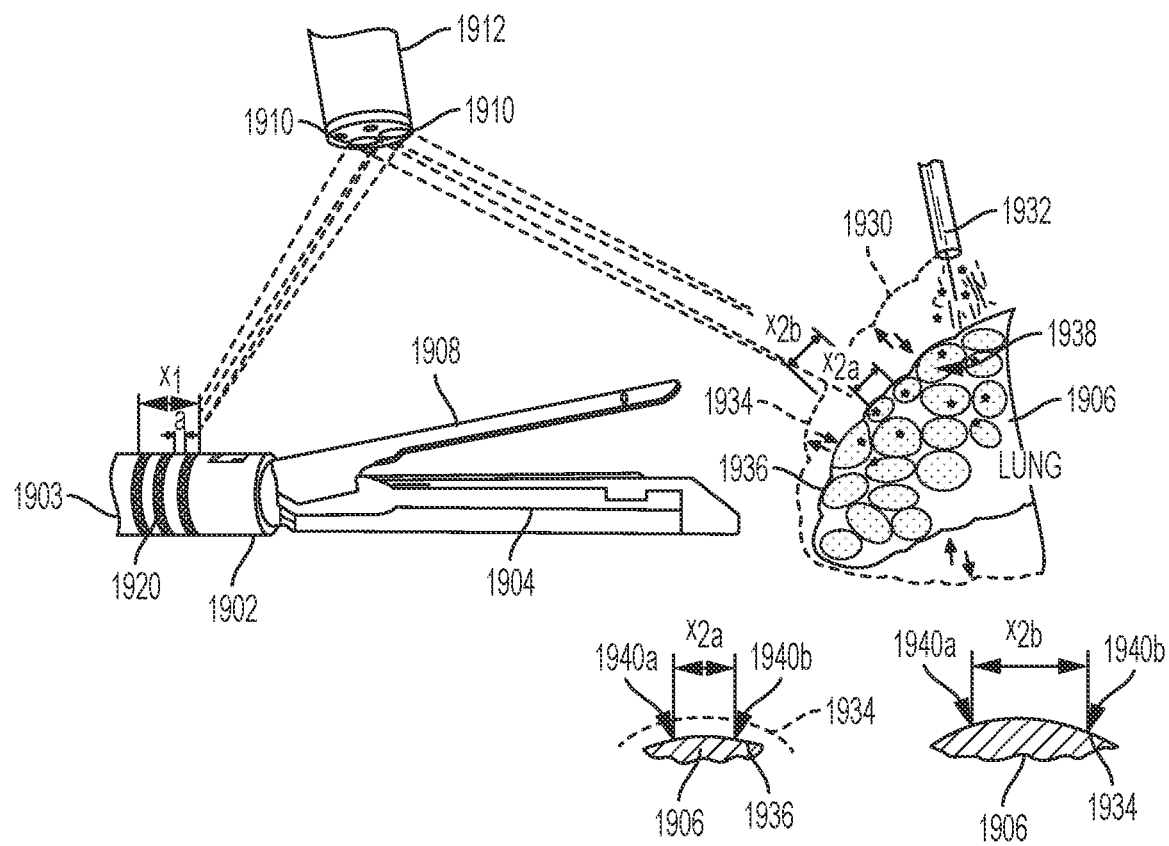
FIG. 7 is a perspective view of one embodiment of a surgical tool with an end effector in the vicinity of patient tissue.

Visual sensors and/or cameras can be used to detect a variety of parameters instead of or in addition to temperature. For example in some embodiments, visual sensors and/or cameras can be used to detect a sensed amount of displacement of a tissue surface, a strain on the tissue of the patient, and/or other inserted tools during an operation. FIG. 7 illustrates a shaft 1903 of an electromechanical tool with an end effector 1904 disposed on a distal end 1902 of the shaft 1903 in the vicinity of patient lung tissue 1906. The robotic system of FIG. 7 is similar to the systems described above. The surgical system can include a controller, such as controller 315 illustrated in FIG. 1, operatively coupled to the shaft 1903 and the end effector 1904, e.g., via an electromechanical arm. In this embodiment, the controller can be configured to retard advancement of the end effector 1904 toward a tissue surface 1930 of the tissue 1906 based on a sensed amount of strain or displacement of the tissue surface 1930.

A binocular scope 1912 can be used to view the shaft 1903 and the end effector 1904. The shaft 1903 can include one or more fixed-size and fixed-space indicators in the form of markers. In the illustrated embodiment, the markers are in the form of spaced annular rings 1920 on the shaft. In other embodiments, markers can be present on the end effector. In the example illustrated in FIG. 7, the end effector 1904 includes a cutting element (not shown) that travels through the end effector 1904. A marker can be placed on the cutting element itself. The binocular scope 1912 can include one or more cameras 1910. Each camera 1910 can obtain a separate image of the shaft 1910 and its markers 1920. Markers 1920 can have a fixed spacing. Each marking within the set of markers 1920 can have a fixed width a, and the entire set of markers 1920 can have an overall fixed width Xi. Because the lengths and widths are fixed and known, the markers 1920 can be used to determine a length scale for images taken by the one or more cameras 1910. An applicator 1932 can apply a material 1938, such as a particulate, onto the tissue surface 1930. The one or more cameras 1910 can image the operating site more than once, and the system can compare the images and compare the relative positions of the material 1938 in successive images. Because the system has a length scale and can determine relative movement of the material 1938 in successive images, the system can use the material 1938 to calculate an amount of displacement of the tissue surface 1930. For example, the displacement can be from a first position 1936 to a second position 1934, as illustrated in FIG. 7 using lung tissue. Two particles 1940*a*, 1940*b* can be disposed on the surface of the tissue 1906. When in a deflated state the system can measure a first distance $X_{2a}$ between the two particles 1940*a* and 1940*b*. When in an inflated state, the system can measure a second greater distance $X_{2b}$ between the two particles 1940*a*, 1940*b* is $X_{2b}$. By comparing the changes in the two states, the system can determine displacement and/or strain on the tissue.

The sensed amount of displacement can allow the system to determine a maximum threshold position related to the measured displacement. For example, the system can compare the inflating and deflating lung tissue in FIG. 7 and determine that, between the first position 1936 and the second position 1934, the second position 1934 represents a maximum threshold position of the tissue. By determining that tissue is at a maximum threshold position at position 1934, the system can affect or alter tool movement to have greater control and precision when interacting with the tissue. The analysis of the movement of the particles can also facilitate determination of period movements of the tissue 1906. Consequently, anticipated organ position can be determined and accounted for during manipulation of tissue and grasping of tissue. Similarly strain or force estimates can be used together with maximum thresholds to avoid over-stretch, over-stress, or tearing of tissue 1906. For example, during lung adhesion dissection, a limit on tissue deformation can be set so that if a user of the surgical system approaches the limit on tissue deformation, the surgical system can sound an alarm and/or generate a visual/tactile/etc. notification to the user to prevent over-stretch. In some variations, the surgical system can be configured to stop the movement of any end effector if a threshold is exceeded.

A variety of different materials and/or particulates can be used. In some variations, the material applied to tissue can be a bio-absorbable aerosolized particulate material and/or a high contrast material. For example, the contrasting particles can be 0.1 to 5 mm in size and made of a biocompatible and absorbable material selected such that they will cause no or limited harm when left within the body. Examples of such materials include absorbable polymers having a short degradation duration, sugars, or similar materials that will degrade and absorb within a relatively short time period. In some variations, materials can be selected that absorb within 24 hours of application to avoid long term inflammatory responses or risk of encapsulation or adhesion promotion. Particulates can be absorbable polymer with dye, can be vicryl like, can include a sealant to ensure the particulates stick to tissue, can be PCA, PLA, PGA, etc. A variety of sizes of particles can be used, including particles that are too large to be applied through an aerosol application. While lung tissue is discussed herein, any tissue at a variety of different operation sites can be used.

The system can compare the relative changes between particulate from successive images and/or can determine an exact measurement of the various changes in displacement using the length scale from the markers 1920. Because the lengths and widths of the markers 1920 are fixed and known, the system can use the binocular scope 1912 with the one or more cameras 1910 to compare and contrast the markers 1920 with the particulate positioning and/or the displacement of one or more particulates over successive images and determine an estimated size of the displacement, for example by using the dual focal length of the scope 1912 when at least two cameras 1910 are present. Similar to the markers discussed above, the controller can also use the markers 1920 and/or the material 1938 to determine a position of the end effector 1904 relative to the tissue 1906. The controller can then retard advancement of the end effector 1904 when the sensed amount of displacement of the tissue 1906 is within a predetermined displacement range, thus preventing accidental collision or less precise interaction between the end effector 1904 and any surrounding tissue.

The material 1938 can thus provide contrast points on the tissue 1906 of the patient, and images obtained by the one or more cameras 1910 can facilitate determination of the movement of the tissue 1906 based on the movement of particles of the material 1938 relative to each other. As mentioned, tissue strain can be determined for the tissue 1906 based on the movement of the particles relative to each other. In some variations, area and volume estimates can be determined based on the positional information. As with positional information, changes in the area and volume of tissue can be determined based on multiple images taken by the one or more cameras 1910 over time.

In various embodiments, particles provided in the material applied to tissue can have a known size and geometry. For example, the geometry of the particles may include geometric shapes, rods with round balls on the ends, or the like. As with the markers 1920 allowing determination of a visual scale, if the size and/or geometry of the particles are known, a distance between particles and movement of the particles can be determined. While a relative distance can be determined between particles, an actual distance between particles and/or of various locations at an operation site can also be determined because of the known size and/or geometry of the particles. This can allow kinematic analysis and interpretation of the relative position and motion of the particles and therefore the tissue. These particles can be used instead of or in addition to markers on a tool. In some embodiments, particulate can allow the system to create topographical representations of tissues and/or operation sites.

In some embodiments, movement of tissue can provide information on which surgical instrument and/or what size instrument to use with the robotic surgical system. For example, in embodiments using a cutting element and stapler in an end effector, a determination of what size stapler cartridge to use can be made. Particulate in combination with markers on a shaft and/or end effector can be used to measure one or more atomic features of the patient, place a scale with the field of view of the cameras, and/or as a safety measure for the surgical system to assure safe stopping of the end effector as the instrument approaches tissue.

In addition to or instead of using markers on a tool to determine a length scale, an array of particles can be disposed on a tissue surface at an operation site to facilitate recreation of a three-dimensional space. For example, a calibration grid generator can be incorporated into the scope 1912 and generate a calibration grid on tissue using a laser-generated speckle pattern of known size and spacing. As with the markers, the known size and spacing pattern can allow the system to make determinations regarding distances and orientations. Because the calibration grid is on the tissue, the system can also make three-dimensional determinations. The laser-generated speckle pattern can be part of the imaging system. The three-dimensional geometry coupled with deformation of the tissue 1906 can facilitate revelation of dissection planes of the tissue 1906 that would otherwise not be detectable in a deflated state.

In some variations, a secondary light source can be used. An example of a secondary light source may include an ultraviolet light source, an infrared light source, or the like. One or more filters can be applied to create the necessary contrast for visualization of tissue. Natural surface features of tissue can be used as trackable objects to further calibrate the surgical system and monitor the movement of tissue. In one example, synthetic particles can be used that are transparent under white light but provide contrast under a secondary light. In this manner, the synthetic particles will not obscure the view of the user of the surgical system. A variety of end effectors can be used herein, such as a cutting element and a stapler for cutting and sealing tissue, clamping jaws with an ultrasonic blade or jaws that deliver RF energy, a suturing end effector, etc. Along with using a variety of end effectors, a variety of additional tasks might be required depending on the end effector used, such as automatically reloading a stapler incorporated into an end effector. U.S. Pat. No. 8,931,682, entitled "Robotically-Controlled Shaft Based Rotary Drive Systems For Surgical Instruments," filed on May 27, 2011, dicloses surgical instruments and is incorporated herein by reference in its entirety. The markers and/or materials and/or particulates and/or grids on tools and/or tissue discussed herein can be used in combination with determining temperatures as discussed herein.

In addition to the safety mechanisms discussed above, additional safety mechanisms are possible. For example, distance thresholds are not the only mechanism possible for limiting movement of an end effector or tool to increase safety of surrounding tissue. A controller can limit large and/or macro motions of an end effector while the end effector is engaged in fine and/or micro activities. For example, if an end effector is being used to suture an incision such that a suturing needle is engaged in tissue, motions and/or activities and/or movements that would not enhance the current activity of driving the suturing needle can be scaled back and/or entirely prevented. In other examples, if an end effector is grasping, clipping, and/or otherwise tethered to tissue, any high speed and/or large motions can be limited or otherwise scaled back until the tissue is released. This mechanism can prevent unintended and/or potentially harmful movement to increase the safety of an operation using the robotic systems provided herein. One or more warnings can be provided to an operator so that the operator is aware of the limitations placed on movement. Similar to above, the warnings can be any of a number of tactile, vibratory, auditory, and/or visual notifications, such as being provided on a screen. The operator can then choose to override the mechanisms if desired based on the specific circumstances of an operation. Because so much of the robotic systems provided herein depend on visual sensors and/or cameras, an automated cleaning process of the visual sensor and/or camera can also be incorporated into any of the systems herein. U.S. Patent Pub. No. 2008/0081948, entitled "Apparatus for cleaning a distal scope end of a medical viewing scope," filed on Oct. 3, 2006, and U.S. Pat. No. 8,915,842, entitled "Methods and devices for maintaining visibility and providing irrigation and/or suction during surgical procedures," filed on Jul. 14, 2008, disclose cleaning processes and are incorporated herein by reference in their entirety. Automated cleaning of the visual sensor and/or camera can occur when foreign material is detected on an image.

There are several general aspects that apply throughout the application. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers.

A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 8:
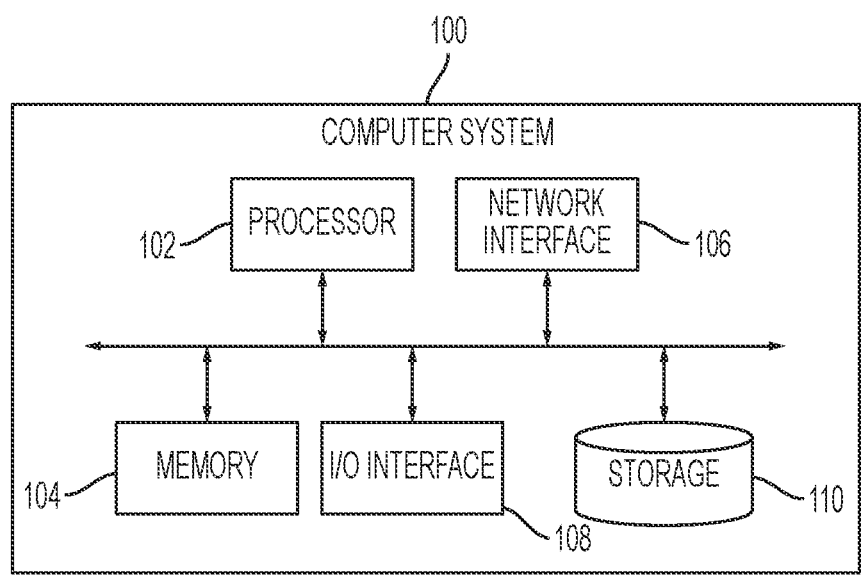
FIG. 8 is a diagram depicting a computer system for facilitating control of a robotic surgical system.

FIG. 8 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 8 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
an electromechanical tool having an instrument shaft and an end effector formed thereon; and
a controller configured to retard advancement of the electromechanical tool toward a tissue surface based on a sensed temperature of the end effector by reducing a velocity of the electromechanical tool to a first threshold velocity when the sensed temperature is within a first predetermined temperature range and to a second threshold velocity when the sensed temperature is within a second predetermined temperature range, wherein the controller is configured to retard advancement of the electromechanical tool when the end effector is within a predetermined threshold distance from a tissue surface, and wherein the predetermined threshold distance varies based on the temperature of the end effector.

2. The surgical system of claim 1, further comprising a sensor configured to sense the temperature of the end effector.

3. The surgical system of claim 2, wherein the sensor comprises an IR sensor.

4. The surgical system of claim 2, wherein the sensor comprises a thermocouple disposed on the end effector.

5. The surgical system of claim 1, further comprising a sensor configured to sense a position of the end effector relative to a tissue surface.

6. The surgical system of claim 1, further comprising a sensor configured to sense a distance of the end effector from a tissue surface.

7. A method of operating a surgical system, comprising:
receiving a sensed temperature of an end effector disposed on an instrument shaft of an electromechanical tool;
reducing a velocity of the electromechanical tool toward a tissue surface to a first threshold velocity when the sensed temperature is within a first predetermined temperature range; and
reducing the velocity of the electromechanical tool to a second threshold velocity when the sensed temperature is within a second predetermined temperature range;
wherein the velocity of the electromechanical tool is reduced when the end effector is within a predetermined threshold distance from a tissue surface, and wherein the predetermined threshold distance varies based on the temperature of the end effector.

8. The method of claim 7, wherein the first threshold velocity is adjusted by a first amount in response to determining that the electromechanical tool is a first threshold distance from the tissue surface.

9. The method of claim 8, wherein the first threshold velocity is adjusted by a second amount in response to determining that the electromechanical tool is a second threshold distance from the tissue surface.

10. The method of claim 7, wherein the temperature is sensed by a sensor on the end effector.

11. A surgical system comprising:
at least one data processor; and
memory storing instructions configured to cause the at least one data processor to perform operations comprising:
receiving a sensed temperature of an end effector disposed on an instrument shaft of an electromechanical tool;
reducing a velocity of the electromechanical tool toward a tissue surface to a first threshold velocity when the sensed temperature is within a first predetermined temperature range; and
reducing the velocity of the electromechanical tool to a second threshold velocity when the sensed temperature is within a second predetermined temperature range;
wherein the velocity of the electromechanical tool is reduced when the end effector is within a predetermined threshold distance from a tissue surface, and wherein the predetermined threshold distance varies based on the temperature of the end effector.

12. The surgical system of claim 11, wherein the first threshold velocity is adjusted by a first amount in response to determining that the electromechanical tool is a first threshold distance from the tissue surface.

13. The surgical system of claim 12, wherein the first threshold velocity is adjusted by a second amount in response to determining that the electromechanical tool is a second threshold distance from the tissue surface.

14. The surgical system of claim 11, wherein the temperature is sensed by a sensor on the end effector.

\* \* \* \* \*